(12) United States Patent  
Bonhomme (10) Patent No.: US 10,227,612 B2
(45) Date of Patent: Mar. 12, 2019

(54) METHOD AND DEVICE FOR CONTINUOUS DRY METHANATION

(71) Applicants: METHA ENR, Saint Aunes (FR); Michel Bonhomme, Saint Aunes (FR)

(72) Inventor: Michel Bonhomme, Saint Aunes (FR)

( * ) Notice: Subject to any disclaimer, the term of this patent is extended or adjusted under 35 U.S.C. 154(b) by 880 days.

(21) Appl. No.: 14/420,715

(22) PCT Filed: Aug. 13, 2013

(86) PCT No.: PCT/FR2013/051938
§ 371 (c)(1),
(2) Date: Feb. 10, 2015

(87) PCT Pub. No.: WO2014/027165
PCT Pub. Date: Feb. 20, 2014

(65) Prior Publication Data
US 2015/0203874 A1    Jul. 23, 2015

(30) Foreign Application Priority Data

Aug. 13, 2012 (FR) ..................................... 12 57782
Dec. 20, 2012 (FR) ..................................... 12 62512
(Continued)

(51) Int. Cl.
*C12P 5/02*      (2006.01)
*C12M 1/107*     (2006.01)
(Continued)

(52) U.S. Cl.
CPC ............. *C12P 5/023* (2013.01); *C12M 21/04* (2013.01); *C12M 21/16* (2013.01); *C12M 23/34* (2013.01);
(Continued)

(58) Field of Classification Search
CPC ........ C12P 5/023; C12M 41/00; C12M 29/06; C12M 21/16; C12M 45/09; C12M 23/34;
(Continued)

(56) References Cited

U.S. PATENT DOCUMENTS 6,083,740 A  *  7/2000  Kodo ..................... B01D 53/84
                                                    435/266
2003/0173291 A1* 9/2003 Schimel .................. C02F 3/006
                                                    210/603

(Continued)

FOREIGN PATENT DOCUMENTS

| CN | 202022920 U | 11/2011 |
|----|-------------|---------|
| FR | 874378 A | 8/1942 |
| FR | 2794472 A1 | 12/2000 |

*Primary Examiner* — Michael L Hobbs
(74) *Attorney, Agent, or Firm* — Patshegen IP; Moshe Pinchas (57) ABSTRACT

A device for continuous dry methanation in a fermenter having a closed tank having at least one compartment to ferment the slurry comprising at least 17% dry matter. An injector to inject pressurized gas close to the bottom of the compartment via at least one chimney that descends through the compartment. The injected gas rising through the slurry creates a convective movement in the slurry around the chimney to stir the matter at the bottom of the compartment. The tank can include a first compartment into which the slurry is introduced and a second compartment into which the hydrolyzed slurry flows after hydrolysis and acidogenesis in the first compartment. Methanogenesis takes place in the second compartment.

8 Claims, 10 Drawing Sheets

(30) Foreign Application Priority Data

Dec. 20, 2012 (FR) .................................. 12 62513
Dec. 20, 2012 (FR) .................................. 12 62514

(51) Int. Cl.
  *C12M 1/00* (2006.01)
  *C12M 1/02* (2006.01)
  *C12M 1/34* (2006.01)
  *C12M 1/16* (2006.01)

(52) U.S. Cl.
  CPC ............ *C12M 29/06* (2013.01); *C12M 29/14* (2013.01); *C12M 29/18* (2013.01); *C12M 29/24* (2013.01); *C12M 41/00* (2013.01); *C12M 41/18* (2013.01); *C12M 41/26* (2013.01); *C12M 45/09* (2013.01); *Y02E 50/343* (2013.01)

(58) Field of Classification Search
  CPC ...... C12M 41/26; C12M 41/18; C12M 29/24; C12M 29/18; C12M 29/14; C12M 21/04; Y02E 50/343
  USPC .................................. 435/290.1–290.4, 292.1
  See application file for complete search history.

(56) References Cited

U.S. PATENT DOCUMENTS

| | | | |
|---|---|---|---|
| 2008/0283468 A1* | 11/2008 | Logan | B01F 3/04517 210/603 |
| 2010/0003717 A1* | 1/2010 | Oyler | C01B 3/50 435/42 |

* cited by examiner

METHOD AND DEVICE FOR CONTINUOUS DRY METHANATION

RELATED APPLICATIONS

This application is a § 371 application from PCT/FR2013/051938 filed Aug. 13, 2013, which claims priority from French Patent Application No. 1257782 filed Aug. 13, 2012, No. 1262512 filed Dec. 20, 2012, No. 1262513 filed Dec. 20, 2012, No. 1262514 filed Dec. 20, 2012, each of which is herein incorporated by reference in its entirety.

TECHNICAL FIELD OF THE INVENTION

This invention concerns a method and a device for continuous dry methanation. It applies in particular to continuous dry methanation in compartments with different physical and biochemical media, by sectoral stirring, at a modifiable high flow rate of gas.

BACKGROUND OF THE INVENTION

Anaerobic fermentation of effluents and waste aims to reduce organic matter and produce energy in the form of biogas. The methanation of sludge in liquid phase coming from the effluent treatment by urban wastewater purification stations, the methanation of the fermentable portion of household waste and the methanation at the farm of manure and other agricultural waste are mainly known. The methanation of effluents from the agrifood industry in liquid phase with a low concentration of dry matter can also be found. Collective co-digestion units, incorporating the treatment of different substrates with different origins (urban, industrial and farming), have been developed.

Fermentation is continuous (matter is continuously or sequentially loaded and unloaded without emptying the digester) or batch (loading of the matter seeded with already fermented matter, with emptying of the digester and reloading with a new substrate).

The person skilled in the art who operates solid substrate methanation plants encounters the limits of the current systems, which methanate with continuous loading, solely for the purposes of mixing fermenting matter in a variable-geometry tank.

The methods for mechanically mixing the matter, moving blades, worm screws, moving cylinder or mixing by a high-pressure or compressed gas, are known. Mixing can be continuous at low pressure or sequential at high pressure, as presented in document FR 2 794 472, in small-diameter pipes or injectors receiving gas at low flow rates and speeds, because of the dispersion over multiple injectors or injection lines with multiple injection openings. Similarly, a digester with several compartments is known. But the known mixing methods, in at least two compartments, do not let slurry close to shear thresholds flow; and they are not suitable for allowing the matter to be stirred in the entirety of a given volume; and they cannot enable control of the fermentation that makes possible significant degradation of the fermenting matter in short retention times and without significant dilution of the matter.

The gas stirring systems that inject gas from the bottom of tanks require an especially large civil engineering structure to access the gas lines exiting at the bottom of the fermentation tank. The lines for intermittently injecting pressurized gas cannot cope with any reflux of matter, which can block the injectors, in the gas pipes. The tip of the injector is necessarily narrow, generating a narrow upwards gas jet that can have only a limited effect on the stirring of slurry; during gas injections this creates preferential passages in the matter that limit the stirring and turning over thereof, in particular for matter at the bottom of the tank, thus making it difficult to put heavy elements back in suspension, with the risk of these accumulating at the bottom of the fermenter. The insufficient stirring thus makes the flow of matter more difficult with phase separations creating dead zones and different fermentation speeds in the fermenter.

It is also noted that the fermentation phases can be sufficiently controlled by significant dilution effects of the matter to boost its flow which also, because of the nature of the stirring, most frequently mechanical or by gas stirring, results in carrying out fermentations in infinitely mixed fermenters. The retention times of the matter are therefore random. There are significant residual liquid effluents at the end of fermentation. For some types of effluent, the lack of dry matter is a factor limiting fermentation through lack of a bacterial medium. This lack of dry matter requires introducing mineral media to fix the bacterial populations that need a medium.

OBJECT AND SUMMARY OF THE INVENTION

The present invention aims to remedy all or part of these drawbacks.

To this end, according to a first aspect, the present invention envisages a method for continuous dry methanation, in a fermenter comprising a closed tank, characterized in that it consists of:
  introducing slurry to be fermented, comprising at least 17% dry matter, into at least one compartment of said tank, and
  injecting pressurized gas, via at least one chimney that descends through at least one said compartment, close to the bottom of the compartment, to create, by the injected gas rising through the slurry, a rising movement in the slurry around the chimney, stirring the matter that is found at the bottom of the compartment.

Preferably, the slurry comprises at least 22% dry matter.

Thanks to these provisions, all the fermenting slurry is stirred, including the portions that tend to settle.

In embodiments, the slurry is introduced into a first compartment and, after hydrolysis in the first compartment, the hydrolyzed slurry is passed to a second compartment where methanogenesis takes place.

Thanks to these provisions, two media are created that are favorable to the different phases of the fermentation and, as a result, the dimensions of the fermenter and the duration of the fermentation are reduced.

In embodiments, the step of passing from the first compartment to the second is performed at the bottom of the tank, the atmospheres of the compartments thus not being in contact.

Thanks to these provisions, the atmospheres of the different compartments can remain favorable to the reactions in progress in these compartments, by their composition and/or by their heat.

In embodiments, during the gas injection, gas from the fermentation of the slurry is introduced.

In embodiments, during the gas injection step, gas is injected into at least two chimneys close to each other.

In this way, stirring fronts are produced that are favorable to the translation movement of the matter undergoing fermentation.

In embodiments, the method that is the subject of the present invention comprises a step of measuring the viscosity of the slurry wherein, during the gas injection step, the quantity of gas, its flow rate and/or its speed are dependent upon the viscosity measured.

In this way, the quantity of gas injected and/or the stirring of the slurry is kept suitable to its actual state in the fermenter.

In embodiments, during the step of measuring the viscosity of the slurry, the slurry's resistance to the injection of gas is measured during the injection of gas.

In embodiments, during the step of measuring the viscosity of the slurry, a duration of a predefined drop in pressure of the injected gas is measured.

Thanks to these provisions, the actual state of the slurry is measured directly.

In embodiments, the fermenter comprises a plurality of chimneys, and, during the gas injection step, gas is injected successively into the chimneys.

In embodiments, during the gas injection step, gas is injected successively into the chimneys going from upstream to downstream on the path followed by the slurry.

Thanks to these provisions, the slurry's movement along the length of the fermenter tank is boosted—made possible by the homogenization of sufficiently hydrolyzed matter.

In embodiments, the method that is the subject of the present invention comprises a step of collecting slurry on the path followed by the slurry, and a step of injecting slurry upstream of the collection point.

The different methanation phases can be boosted in this way, by adjusting the pH and/or the bacterial colonies of the tank's various sectors.

In embodiments, during the gas injection step, a gas is injected into the slurry that has a pressure at least five times, and notably five to ten times, higher than the pressure at the height of the column of matter around the chimney, and at least 4 relative bars, according to the viscosity.

This thus causes significant stirring.

In embodiments, the method that is the subject of the present invention alternatively comprises:
- a step of injecting gas into the slurry, and
- a step of compressing biogas in a pressurized storage chamber.

In this way, the fermenting matter is left to rest between two injections of gas and a small-sized compressor can be utilized.

In embodiments, the cyclic ratio between the gas injection duration and the compression duration is less than one-thirtieth.

According to a second aspect, the present invention envisages a device for continuous dry methanation, in a fermenter comprising a closed tank, which comprises:
- a means of introducing slurry to be fermented, comprising at least 15% dry matter, into at least one compartment of said tank, and
- a means of injecting, via at least one chimney that descends through at least one said compartment, pressurized gas close to the bottom of the compartment, configured to create, by the injected gas rising through the slurry, a rising movement in the slurry around the chimney, stirring the matter that is found at the bottom of the compartment.

As the particular features, advantages and aims of this device are similar to those of the method that is the subject of the present invention, they are not repeated here.

BRIEF DESCRIPTION OF THE DRAWINGS

Other advantages, aims and characteristics of the present invention will become apparent from the description that will follow, made, as an example that is in no way limiting, with reference to the drawings included in an appendix, in which.

DETAILED DESCRIPTION OF EMBODIMENTS

After having noted that the figures are not to scale, and before describing the figures in more detail, a description of characteristics of particular embodiments of the method and device that are the subjects of the present invention is given below.

Continuous methanation of slurry is carried out in a compartmented vessel at two temperature and pH levels, based on a sector-modifiable stirring, according to the viscosity of the fermenting matter, by injecting gas at high speeds and flow rates, in several chimneys. The configuration of these creates a broad convective movement starting from the bottom of the fermenter, drawing the matter over a large surface.

The mixing of a slurry is preferably sectoral. The stirring of a matter close to the flow thresholds by injecting pressurized gas presents limits. The limits encountered in the prior state of the art are of two types, depending on whether the substrates are diluted or one operates in a mode called dry or slurry:
  the necessity of very significantly diluting the dry substrates from 25% dry matter to 8%, 10% dry matter, requires the intake of additional liquid, which is most often taken from the excess liquid portion on output from the fermenter. The recirculation of excess "percolates" for diluting the incoming substrates necessarily involves phenomena inhibiting fermentation through the concentration of mineralized nitrogen, for example progressively alkalinizing, i.e. increasing the pH of, the fermentation medium and thus limiting hydrolysis and acidogenesis.

fermentation on slightly diluted or undiluted substrates in continuous fermentation with high levels of dry matter encounters other limits that lie mainly in control of the fluid mechanics.

In the prior state of the art, the limits of stirring a slurry and of its flows, with a significant impact on the fermentation processes, can be observed. The first difficulty is to mix a slurry from bottom to top over the height and over a broad sector of matter; the mixing or stirring by gas must be sufficiently powerful to stir a slurry in a defined sector and volume. The particularity of a gaseous flow, necessarily starting from a low point, is to expand during its rise and consequently to leave the lowest portion of the matter to be stirred outside the mixing movement.

This leads to unmixed zones in the lower portion of the gaseous flow and on the periphery of the fermenters because of the loss of load due to friction of the matter hitting the walls. Thus, on the bottom of fermenters, over a more or less substantial thickness, there are found sediments of heavier elements and the accumulation of unmixed matter, in particular in the space between two gas jets and at the periphery of the fermenters in areas close to the walls.

The limits encountered by all the systems of mixing with gas by pipes, injectors in the bottom of the tank or mixing lines for stirring in infinitely mixed or slurry mode have impacts on the biochemical and biological operation of the fermenters of the previous state of the art.

These "dead" zones of sediment accumulation are created and enlarge over time. The solid-liquid contact necessary for biological activity is made difficult. This disrupts the bacterial balances. Without hydrolysis, the viscosity of the matter remaining very high makes the passage from one compartment to the other difficult.

The operation with a slurry, therefore with a high level of dry matter in the fermenter, can only take place with a matter that is hydrolyzed, in an acidic medium, making possible the solid-liquid exchanges, substantially mixed and at a sufficiently high temperature to reduce the viscosity.

We know the great impact of the temperature associated to the pH, which changes the viscosity and the structure of the organic matter necessary for stirring and homogenization, and also has an impact on the selective development of bacteria and on the process of degrading and transforming the matter.

Which encourages a move towards hyperthermophilic temperatures for boosting hydrolysis and acidogenesis, while taking into consideration the fragility of methanogenic bacteria to hyperthermophilic temperatures and acid pHs.

The same level of temperature and pH in the phases of hydrolysis, acidogenesis, on the one hand, and of methanogenesis, on the other hand, limits the continuous fermentation of slurry.

We emphasize the necessary interaction, for the continuous methanation of slurry, between the physical devices belonging to fluid mechanics and rheology and the biochemistry of the fermentation inducing the selectivity and development of the bacterial populations or inhibition phenomena.

The originality of the embodiments of the present invention is to be able to operate continuously with slurry, or in other words in dry mode, in two compartments having different pHs and levels of temperature.

The term "dry mode", commonly used, is in fact inappropriate since even very thick matter with a high level of dry matter comprises a humid portion, present in the cells of the matter to be fermented, which is quickly released by the enzyme activity and the increase in the temperature of the medium. This liquid portion, outside the solid structure of the substrate, is necessary for exchanges of metabolites that dissolve in the humid portion to be accessible to the bacteria. Slurry therefore needs a more detailed definition. Before entering the fermenter, the matter is solid, shovellable, i.e. it can be moved with a mechanical shovel, and does not flow; just a liquid percolate may possibly seep out from the mass and trickle. This is a non-Newtonian fluid, which can be characterized as a threshold fluid, close to the shear threshold, elastic and viscous. When the substrate is too solid— e.g. more than 25% dry matter for manure or more than 30% dry matter for the fermentable portion of household waste— it has to be slightly diluted with a liquid effluent, water or a liquid derived from the downstream treatment of the digestate, a liquid collected by pressing, evaporation with liquid distillate produced, or some other process separating the solid phase from the liquid phase.

The matter, after possibly being slightly diluted before entering the fermenter, is introduced into the fermenter via a chimney, or any other introduction device such as a worm screw, to be mixed with the fermenting matter in hydrolysis phase that is present in the first sector of the first compartment, operating at a hyperthermophilic (65° C.), or thermophilic (55° C.), temperature level. Stirring a very thick matter that is mixing with matter already present in the first portion of the fermenter and that has undergone thermo-enzymatic hydrolysis is beneficial for the method. The viscosity of the matter is modified under the influence of the thermo-enzymatic hydrolysis (combination of the temperature and the enzymatic action of the bacteria).

The stirring system is beneficial for the method's entire operation. In particular, the device makes it possible to homogenize different substrates with solid elements, e.g. straw fibers, and more liquid elements consisting of elements that are soluble or in suspension, such as slurries, and heavier elements, e.g. gravel, stones. Homogeneity boosts the flow of a slurry in the first compartment, which slurry liquefies with hydrolysis, and then in the different phases of fermentation while nevertheless remaining thick. Homogenization and liquefaction in the first compartment boost passage through a separation wall between two compartments. The effectiveness of the stirring is also necessary for homogenizing different temperatures in the two compartments with thick substrates having low thermal conductivity. In embodiments, the fermenting matter is extracted at different points of the fermenter to be reintroduced at other points of the fermenter by chimneys in order to inoculate a sector with bacterial colonies coming from another sector. Similarly, by reintroducing fermenting substrate from one sector into another sector, the biochemistry of the second sector can be balanced by acidification or alkalinization.

The present invention utilizes, in embodiments:

control of the modifiable stirring of a slurry with a high level of dry matter, with 17% to 30% dry matter, sector by sector, according to the changing viscosity of the fermenting substrate, in a compartmented fermenter, and regular progression and flow of a thick homogenous substrate, required for the balance of the hydrolysis, acidogenesis and methanogenesis phases, and interaction between the methods of stirring a slurry and the control and management of the phases of continuous methanation of slurry.

The fermentation device that is the subject of the present invention comprises a closed fermentation vessel comprising at least two compartments and a set of chimneys having a sufficiently large diameter, e.g. between 80 mm and 150 mm, distributed throughout the fermenter and defining mixing sectors of the fermenter. Each chimney starts at the ceiling of the vessel and plunges into the fermentation vessel until close to the bottom of the vessel, preferably less than 15 cm from the bottom.

Preferably, the gas injection chimneys are configured to extend from the ceiling of the vessel, or tank, over at least 97% of the height separating the ceiling from the bottom of the vessel, and preferably at least 98%.

Preferably, the stirring of a slurry is performed by sector by injecting, into at least two chimneys having a large enough diameter, a significant quantity of gas, preferably biogas from the methanation, at a flow rate of between 2,000 $m^3$/hour and 6,000 $m^3$/hour, during a short period of time, for example between 10 and 15 seconds. The gas injection, which is carried out at a high flow rate and speed, from top to bottom from the ceiling down to a short distance from the floor, hits the floor, thus creating a cone of gas on the floor and a large rising column of gas, expanding as it rises, up to the high point of the matter, generating a swelling 208 (FIG. 8) followed by significant waves, the cone of gas vacuuming up, especially from the bottom, at the bottom of the fermenter, the matter, which enters into a convective movement with a radius of 1.5 m to 2 m, in an area surrounding the rising gas column and thus creating a sweep of the bottom in an equivalent radius, 210 and 211 (FIG. 9). The radius of the truncated portion of the cone of gas is a function of the speed, the flow rate of the gas and the viscosity of the matter.

Stirring a slurry over the matter's entire height, in a defined sector, is made possible by means of a compressor, a chamber of high-pressure gas, the chimneys starting at the ceiling to emerge very close to floor, receiving gas by gas injected from top to bottom, over a short period.

The chimneys are, most often, arranged at least in pairs to take into consideration the shear load generated by the friction of the fermenting matter on the two walls channeling the matter in its plug-like progress, walls delimiting the flow of matter flowing from one sector to another.

Figure 8:
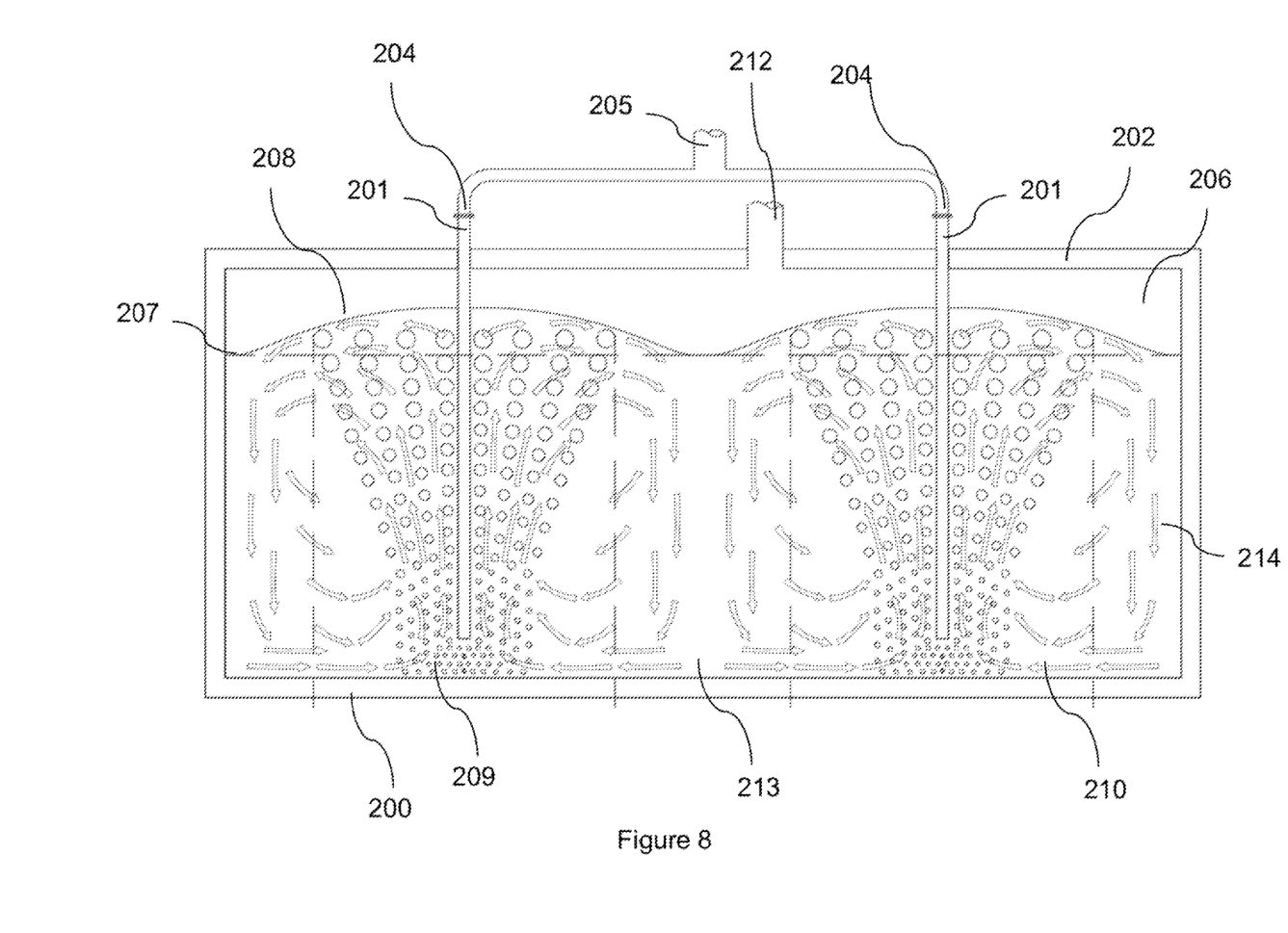
FIG. 8 represents, schematically, in a transversal cross-section, flows in particular embodiments of the stirring device that is the subject of the present invention.
Figure 9:
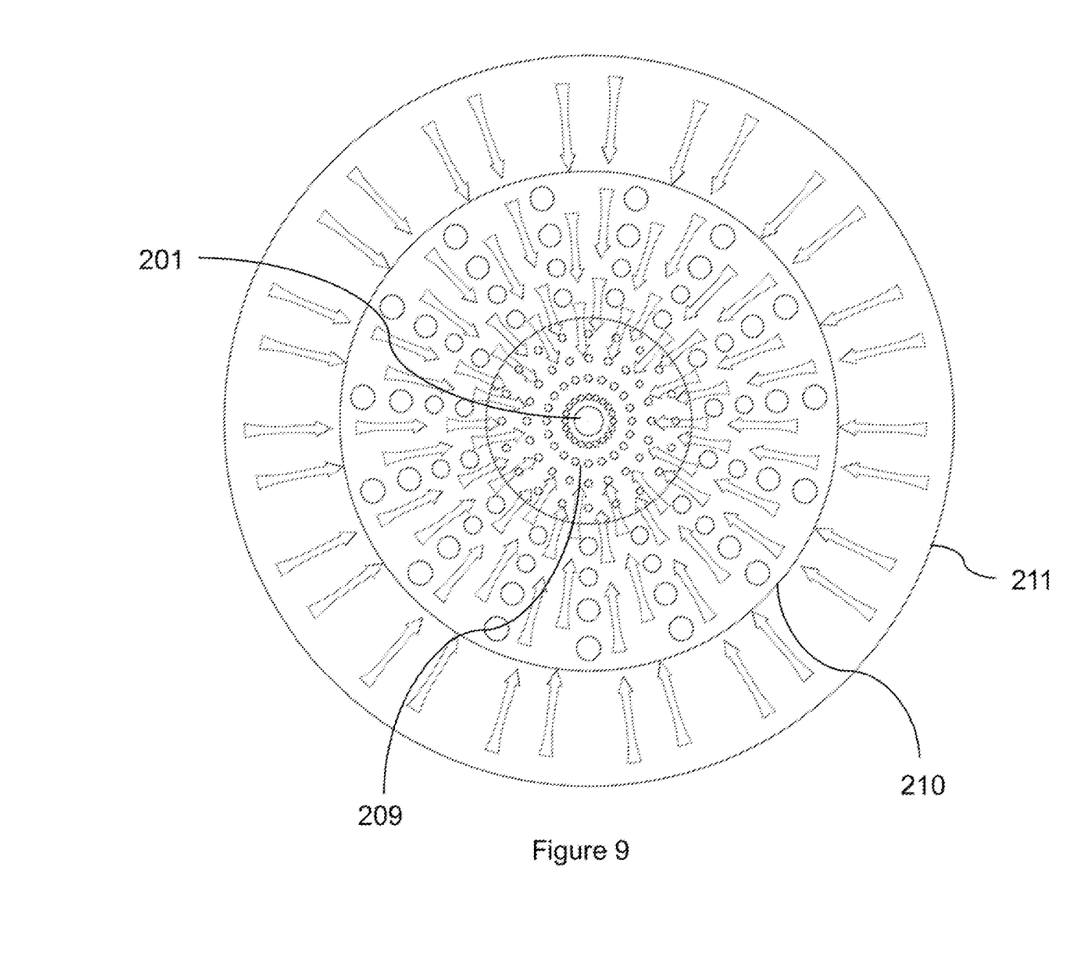
FIG. 9 represents, schematically, in a bottom or top view, gas-matter flows from sector to sector in particular embodiments of the fermentation device that is the subject of the present invention.
Figure 10:
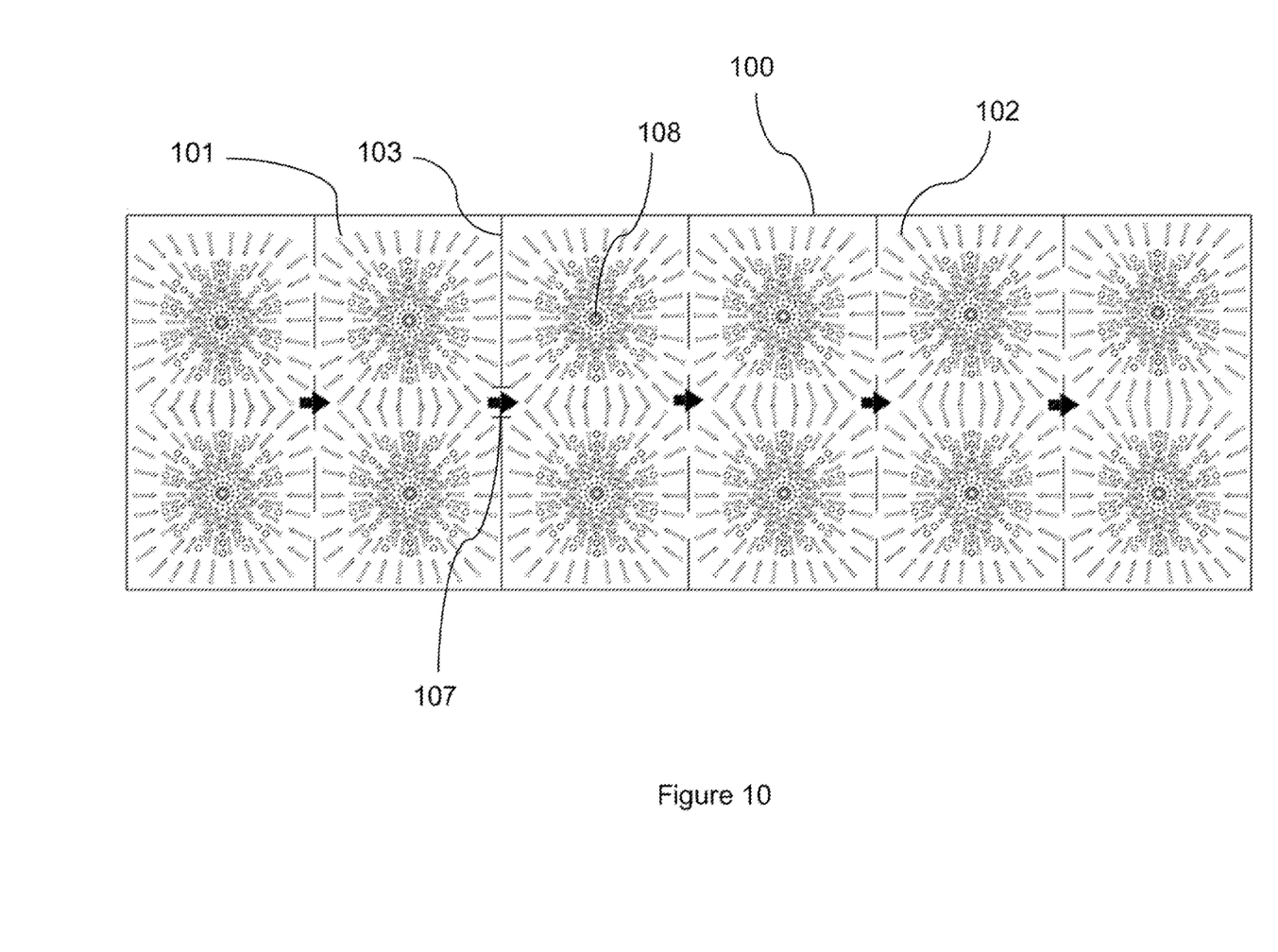
FIG. 10 represents, schematically, in a bottom or top view, gas-matter flows from sector to sector in particular embodiments of the fermentation device that is the subject of the present invention.

Each pair of chimneys is separated from another pair of chimneys by a defined distance 213 (FIG. 8). Widthwise, the sector is equipped with at least two chimneys arranged at a given distance from the wall, the wall generating a loss of load and modifying the range of the convective movement. The loss of load requires the chimneys to be close to the walls to avoid having areas that are not sufficiently stirred. Since there are necessarily two walls channeling the pathway of the matter, there are therefore at least two chimneys. In the direction of movement of the matter (FIG. 10), the distance between two pairs of chimneys is greater since the expansion of the gas and the matter's movement are not limited by a wall. This allows wider expansion of the matter's convective movement. Thus, as an example, for a passage four meters wide and five meters high, the two chimneys are positioned 70 cm from the walls and they are 2.6 meters from each other. The distance between each pair of chimneys is defined by evaluating the convective movement and its modification as a function of the speed and flow rate of the gas injected. The distance separating two pairs of chimneys is, for example, three meters, the convective movement of each pair of chimneys having a radius of 1.5 meters, the movement being modified and controlled by the speed and flow rate of gas at the mouth of the chimneys, the speed and flow rate being modified as a function of the viscosity of the matter, the viscosity being set by the variations in duration of a given injection. These variations indicate the dynamic viscosity of the matter according to the physical and biochemical parameters in the fermentation process.

The speed and flow rate of gas injected into the chimneys depend on the width of the matter's front, a variable width in a cylindrical digester channeled by at least two walls, one transverse wall dividing the flow of matter in two and one vertical wall delimiting a first compartment separating both the matter and the overlying gas-filled space of the second compartment, letting the matter pass by a wide opening in the lower portion of the vertical wall.

Some chimneys intervene separately, in particular those located in a reduced front or close to a narrower passage of fermenting matter. These chimneys have a more limited impact on the matter-stirring zone, taking into account the closeness of the walls and the loss of charge that accompanies it.

As shown in FIG. 8, thanks to the buoyancy exerted on a significant volume and flow rate of gas around two chimneys 201, the speed and the flow rate define the width of the stirring of a given sector as a function of the viscosity of the matter.

The injection can be modified according to the viscosity of the matter. The stirring of a sector by injecting gas from a chamber with a defined volume, the injection presenting a flow rate and a speed, is modified by the pressure level at which the gas is released, as a function of the viscosity of the fermenting matter, which viscosity is governed by the variations in duration of a given injection. The greater the viscosity, the longer the duration of an injection of gas.

The injection of 30 $m^3$ of gas with a decreasing pressure in the chamber of between seven and four bars for example, in two chimneys is of the order of 17 seconds in the first sector of the first compartment but reaches 12 seconds in the last sector of the second compartment.

As a function of the matter, depending on the fermentation sector, the speed and the flow rate of the gas injected from the pressure chamber are modified. For example, the pressure of the gas in the 10 m3 chamber is raised to 7 bars to be held at 7 to 4 bars, namely 30 $Nm^3$ of biogas in the first sector of the first compartment where the viscosity of the matter is high, whereas the pressure of the gas is raised to 6 bars, to be held from 6 to 3 bars, namely 30 $Nm^3$ of biogas in the last sector of the second compartment where the viscosity of the matter has significantly decreased under the action of the hydrolysis and fermentation.

The modification boosts the fermentation process. With insufficient speed and flow rate, the stirring and convective movement of the fermenting matter in a given sector would be insufficient and would generate preferential passages of matter flowing and dead zones of matter unable to flow. With too high a speed and flow rate, significant zones of overlap from one sector to another would be observed. Particles would be carried from one sector to another at each stirring cycle to exit rapidly from the fermentation tank, thus resulting in too short a retention period for some particles and too long a retention period for others.

In embodiments, thanks also to a first wall inside the vessel starting from the ceiling of the vessel, two compartments are created whose overlying gas-filled spaces are separated. This wall leaves a passage in the lower portion for the matter to pass from a first compartment, where hydrolysis/acidogenesis is carried out, towards the second compartment, where acetogenesis/methanogenesis is carried out.

The continuous sectoral mixing of slurry makes it possible to realize in at least two compartments a significant degradation of the organic matter, in a process making possible significant hydrolysis of the matter to be digested and respect of the bacterial populations in each of the fermentation phases, populations developing in different biochemical media (first compartment with acid pH and hyperthermophilic temperature, second compartment with neutral, or slightly alkaline, pH and thermophilic or mesophilic temperature) producing and consuming different metabolites—volatile fatty acids, ethanol, $H_2$, $CO_2$, Acetates, $CH_4$ etc.

The methanation is optimized in a device made of two compartments allowing the different phases of a slurry's fermentation to take place in biochemical media favorable to the matter degradation processes. In particular, the hydrolysis of the incoming substrates takes place in an acidic medium and a hyperthermophilic temperature, allowing the simplification of molecules of complex organic matter made available to the activity of acidogenic bacteria. The acidogenic bacteria, being more resistant than the methanogenic bacteria, develop favorably at an acid pH.

The first compartment, hydrolytic/acidogenic, makes it possible to solubilize the complex molecules to make them available to the acidogenic bacteria that produce, in particular, volatile fatty acids, hydrogen ($H_2$) and carbon dioxide ($CO_2$).

The carbon/nitrogen ratio is preferably of the order of 15 to 25 for good balance of the fermentation. It depends on the actual availability of the carbon, in particular of the carbon trapped in the lignin. A low ratio risks causing an increase in ammonia that can be toxic. With a high pH, for example between 7.4 and 7.6, the mineralized nitrogen in the form of ammonium ions is transformed in part into more volatile ammonia. At high concentration, the ammonia becomes an inhibiter of methanogenesis. The loss of nitrogen is a lack for the agricultural reuse of digested matter, also called "digestate". Hence the benefit of precisely controlling the fermentation phases, in particular a good hydrolysis making available the carbon favoring a better balance of the carbon/nitrogen ratio and, thus, good control of the pH in a range of 6.8 to 7.4 in the second compartment, a range not very favorable to the passage of ammonium in the form of ammonia. This balance makes better nitrogen conservation possible.

In the field of continuous anaerobic fermentation of a substrate with high levels of dry matter, multiple shapes of digesters are known, cylindrical, parallelepipedal, in channels, multi-stage that use either mechanical means for transferring the matter or means of stirring the matter with biogas under pressure. The present invention is not limited to any one of these shapes.

The present invention thus counters the limits encountered in continuous anaerobic processes with a high concentration of matter. It provides, in some embodiments, a method that consists of a plant for continuous anaerobic fermentation, with a high concentration of dry matter, multiphase, mono- or multi-substrate, with slurry, in a single fermenter enabling control of the balance of the hydrolysis, acidogenesis and methanogenesis phases and the matter retention time differentiated according to the nature of the substrates, by the regular progression and flow of a thick, uniform substrate with a high level of dry matter, from 15% to more than 30% dry matter.

With respect to the plug-like flow, a second matter channeling wall (117 in FIG. 4), whose shape depends on the geometry of the fermentation vessel, makes it possible to reduce the front of matter, favoring a steady advance of matter.

The sector-modified stirring of the matter throughout the fermentation process allows the extraction of fermenting matter and its recirculation through the chimneys as bacterial inoculum and biochemical regulator from one sector to another. This inoculum can be extracted at different points of the fermenter in an outlet sufficiently large to allow the passage and flowing of matter, more or less hydrolyzed and fermented and therefore more or less thick, by gravity for collecting by a slurry pump and reintroducing from a given sector to another sector by a chimney equipped with a gas valve and a matter valve, most often upstream. The function of this recirculation, if required, is to reinforce the bacterial activity by reintroducing, into an upstream sector, bacteria produced in a downstream sector or for biochemical rebalancing from one sector to the next.

FIGS. 1 to 7 and 10 show a fermentation vessel 100, a first compartment 101, a second compartment 102, a wall 103 for separating matter, a ceiling 104 of the fermenter, an overlying gas-filled space 105 of the first compartment 101, an overlying gas-filled space 106 of the second compartment 102, a passage of matter 107 between the first compartment 101 and the second compartment 102. For example, the passage 107 measures 50 cm×50 cm.

FIGS. 1 to 7 and 10 also show gas injection chimneys 108, an inlet 110 of matter into the vessel 101 of the fermenter, an outlet 111 of matter from the vessel 100 of the fermenter, a system of introducing slurry (e.g. by a pump) 112, a pipe for recirculating acidic matter 113, a pipe for recirculating fermenting matter 114, a level of matter 115, a pathway partition 117 for matter, a passage of matter 118, an outlet 119 of gas from the overlying gas-filled spaces of the compartments of the fermenter, a pipe 120 of gas towards a gasometer 121 at normal pressure, a pressurized chamber 122, pressurized gas pipes 123, a cogeneration unit 124, a booster compressor 125, a mixer 131.

FIG. 8 shows, in a vessel 200, chimneys 201, a ceiling of fermenter 202, a pressurized gas pipe 205, gas valves 204, an overlying gas-filled space 206, a level of matter before injection 207, a gas discharge level 212, a bottom 213 of the fermenter and a surface blend profile 214.

The device shown in these figures utilizes in particular a plurality of chimneys 108 and 201 distributed throughout the fermenter, with a sufficiently large diameter, e.g. between 10 and 15 cm in diameter, starting from the ceiling of the fermenter and stopping at least 15 cm from the bottom of the fermenter, for example.

The chimneys 108 and 201 are distributed throughout the fermenter at a rate of one chimney per 4 to 10 $m^2$ of floor surface, for example, according to the volume and geometry of the fermenter. The spacing between the chimneys 108 and 201 is a function of the stirring cone generated by the gas injected at the pressure of 4 to 10 bars, for example, by a sufficiently large pipe 205, with a diameter close to that of the chimneys, so as to favor a speed and flow rate of gas arriving at the base of the chimney high enough to perform the stirring of the sector to be homogenized. The flow rate and speed depend on the surface area of the sector to be homogenized, the volume of matter, the height of matter in the fermenter and the wished-for interaction with the other nearby sectors. Some chimneys can be advantageously located at the edge of the walls and partitions of the fermenter to compensate for any potential homogenization problems due to the effect of the walls and partitions.

The gas at several bars of pressure coming from gas stored in a pressurized chamber 122 feeds the chimneys 108 and 201 by a gas duct 205.

As shown in FIG. 8, by buoyancy, gas 209 exerts an upward force on the matter around the chimney 201, which is accompanied by large-size gas bubbles creating a convective movement. The significant difference in density between the gas 209 and the matter causes a convective movement of the matter in a larger zone than the zone of the direct influence of the gas 209, in zone 210.

A large volume of matter is moved by upward force thanks to the bubbles of gas that ascend, thus creating a convective movement of the matter initiating a descending movement in a larger zone by suction of the matter in the lower portion around the chimney 201. This gas-matter convective movement depends on the flow rate and pressure of the gas 209 injected at several bars via the top, most commonly, of at least a pair of chimneys.

The gas 209 arriving near the floor of the fermenter exerts a lateral force that is felt over the truncated surface of the mixing cone with a radius of 0.5 to 1.5 meters for example around the chimney 201, also creating an effect stirring the bottom, as shown in FIG. 8. This stirring is accentuated by the vortex synergy created by the injection of pressurized gas into several nearby chimneys 201 activated at the same time. This movement also causes a swelling of the matter and surface waves, particularly effective and preventing any production of crust created by fibrous matters, such as straw.

The volume of gas compressed in the chamber 122, from ten to thirty m$^3$, for example, between four and ten bars, for example, is a function of the volume of fermenter, and mixing parameters. The volume of gas 209 released from the chamber can be variable and, for example, during an injection of gas 209, pass from six to four bars or from seven to five bars depending on the volume, on the wished-for speed of gas 209, on the height of matter in the fermenter, and on the latter's viscosity.

Each sector is activated successively once the separation of the liquid/solid phases is engaged in the fermenter. This separation of the solid and liquid matters is very slow in a thick medium with a high concentration of dry matter. A complete stirring cycle, over the entire fermenter, takes several hours and can be activated several times a day, for a longer or shorter time depending on the viscosity of the matter in the sector in question.

The sequential compression of the gas thanks to a booster or compressor 125 in the chamber 122 containing the pressurized gas, during a long enough period (several tens of minutes), between two instances of the release of pressurized gas into the fermenter, between ten and twenty seconds, for example, in a defined sector by chimneys 108 or 201, allows the power of the compressor 125 to be reduced significantly by a ratio of approximately 100.

Each sector is defined by at least two chimneys receiving the pressurized gas coming from the chamber 122. Each chimney 108 or 201 in a sector to be stirred can be activated together with other chimneys 108 or 201 of the same sector and receive pressurized gas from a gas pipe 112 and 205 feeding several chimneys 108 or 201 at a time.

The gas injected into the chimney or chimneys 108 or 201, emerging into the overlying gas-filled space of the fermenter to be naturally transferred by a channel 212 into a flexible reservoir or gasometer 121. Then, a portion of the gas present in the gasometer 121 is taken by a compressor 125 that compresses the gas in the chamber 122 before a new injection into a new sector.

Some chimneys 108 allow a recirculation of fermenting or fermented matter into varied points for inoculating bacteria or biochemically balancing some sectors.

Matter is introduced and recirculated thanks to a slurry pump 112, for example of screw pump, concrete pump or worm pump type. The fermenting matter is recirculated by means of matter pipes 113 and 114, for example, which allows a fermenting acidic matter 113 or a fermenting methanogenic matter 114 to be recycled. The device also comprises a first wall 103 separating two compartments 101 and 102 in the chamber 100 of the fermenter. This wall 103 rises up to the ceiling of the chamber 100 of the fermenter, making the overlying gas-filled spaces 105 and 106 of compartments 101 and 102 independent. The wall 103 is open at the lower portion by the passage 107 of the fermenting matter from the first compartment to the second compartment. Thanks to the hydrolysis and homogenization caused by stirring, the passage of the matter is performed simply by gravity generated by the input of new matter, according to the hydrostatic law of fluids (balancing of levels), after stirring if required, from the acidogenic sectors of the first compartment 101.

This wall 103 makes it possible to have, in the same chamber 100 of the fermenter, two different temperature levels, to be able to operate in the first compartment, in thermo-enzymatic hydrolysis, of the order of 65° C., and in the second compartment, mesophilic, of 38 to 40° C., for example, even thermophilic. The first compartment 101, hydrolytic/acidogenic, makes it possible to solubilize the complex molecules to make them available to the acidogenic bacteria that produce, in particular, volatile fatty acids, ethanol, hydrogen and carbon dioxide. The pH of the medium reduces between 5 and 6 for example, without going below 4.5, depending on the substrates, before the methanogenesis phase of the second compartment, where the pH is brought to a level close to neutral thanks to the action of the different methanogenic bacteria families transforming the volatile fatty acids, hydrogen and carbon dioxide into biogas formed essentially of methane and carbon dioxide and mineralizing the nitrogen.

Managing the fermentation by means of pH levels and the level of $H_2$ in the overlying gas-filled spaces and in soluble phase in the substrate (partial $H_2$ pressure), in each compartment is made possible by the separate recirculation of fermenting or fermented matter in different locations of the fermenter by means of chimneys. This management of pH and $H_2$ levels according to the bacterial activity of different bacterial families favors the speed and level of degradation of the organic matter into $CH_4$ and $CO_2$, and the reduction of the matter's retention time in the fermenter. Thermo-enzymatic hydrolysis allows the carbon trapped in the lignin to become available for acidogenic and methanogenic fermentation and to favor a better carbon-nitrogen balance, in particular in straw manure. The partition 103 thus allows the hydrolysis-acidogenesis phases to be controlled separately from the methanogenesis.

The two different temperature levels are managed by a system of heat exchangers supplying calories to the hyper-thermophilic operation of the first compartment 101 and able to extract the surplus calories in the second compartment 102 due the input of fermenting matter with a higher temperature coming from the first compartment 101. However, the surplus temperature of the first compartment 101 can be sufficient to compensate for the energy losses through the fermenter's walls throughout the fermenter.

The first compartment 101 is equipped with a channel for extracting the matter just before the passage of the acidogenic matter 113 to be able to recirculate a portion of the biomass of the acidic substrate into the mixer 131 with the new substrate or directly into one of the chimneys 108 with the help of a slurry pump 112.

The wall 103 defines the volume of the first compartment, which represents between one-sixth and one-quarter of the total volume of the fermenter, for example. In a variant, the wall 103 stops some tens of centimeters, for example, from the bottom of the fermenter leaving a passage over the entire base of the wall. This wall is adjusted according to the geometry of the fermenter. In another variant, the passage 117 is the subject of a lock system that can, as required, close the passage between the compartments 101 and 102. Closing can be actuated from outside the fermenter by introducing, in a slot positioned on the fermenter, a plate blocking the passage. This lock system, which must only be actuated when the fermenter is started up or if matter toxic for fermentation is accidentally introduced, can also be mechanized.

Depending on the fermenter's size and geometry, the fermenter can also comprise a second wall 117 channeling the matter in its pathway from a point of input into the fermenter through to its extraction from the fermenter according to the retention time. The front of matter is thus reduced and the pathway extended by a factor of about two. The front of matter moves from the point of introduction 110 to the point of extraction 111. This also makes it possible to not mix the main bacterial populations that operate at a defined stage of the process and thus do not enter into competition. This second wall 117 rises up to the top of the fermenter in the first compartment 101, separating the overlying gas-filled spaces of the two compartments and does not rise up to the ceiling in the second compartment 102, thus leaving an overlying gas-filled space entirely free on each side of the wall 117.

This variant of the present invention is particularly suited to large capacity installations and for cylindrical fermenters. This wall 117 can be eliminated for rectangular fermenters where the length is greater than the width.

Figure 1:
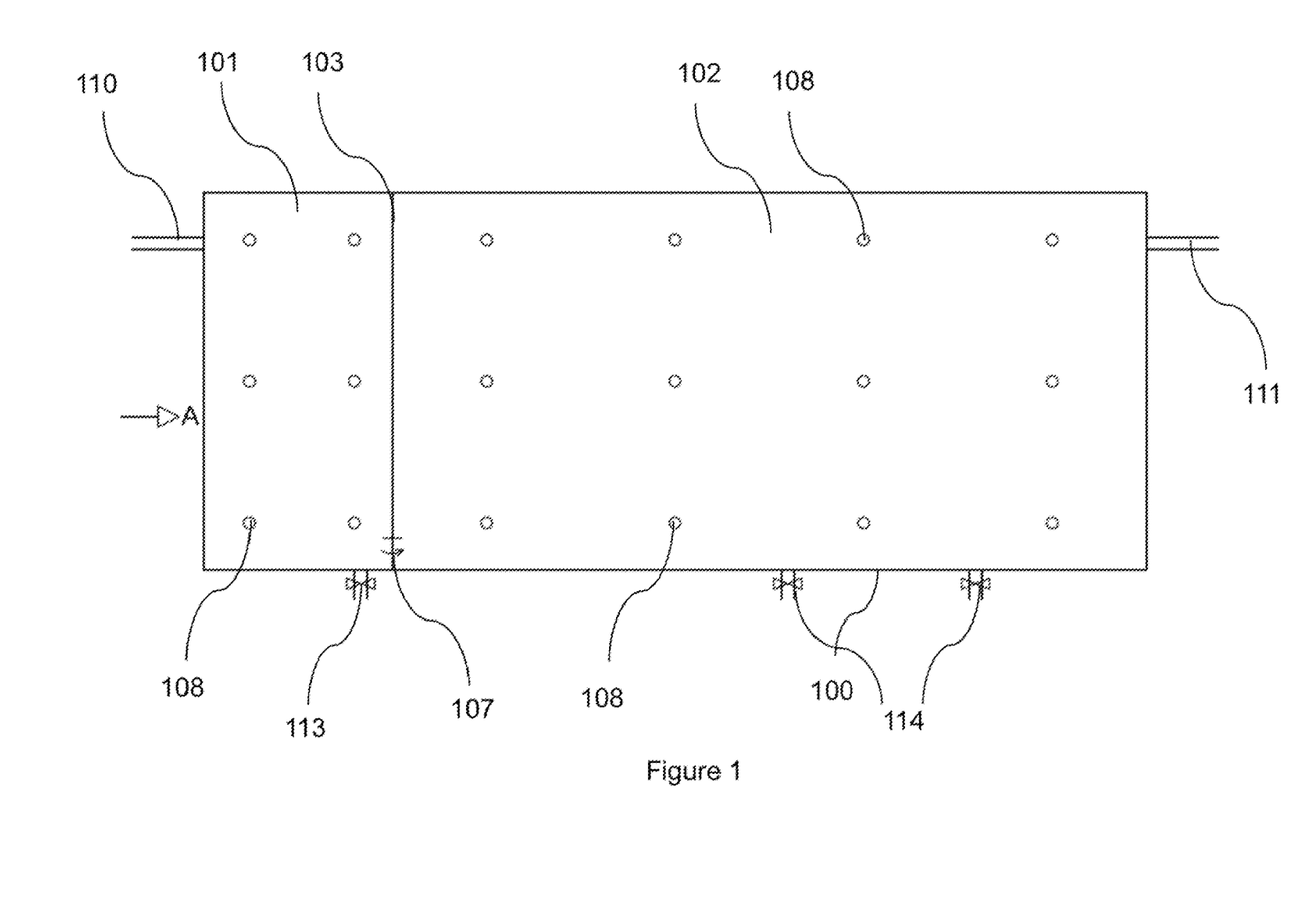
FIG. 1 represents, schematically, in a top cross-sectional view, a first particular embodiment of the fermentation device that is the subject of the present invention.
Figure 2:
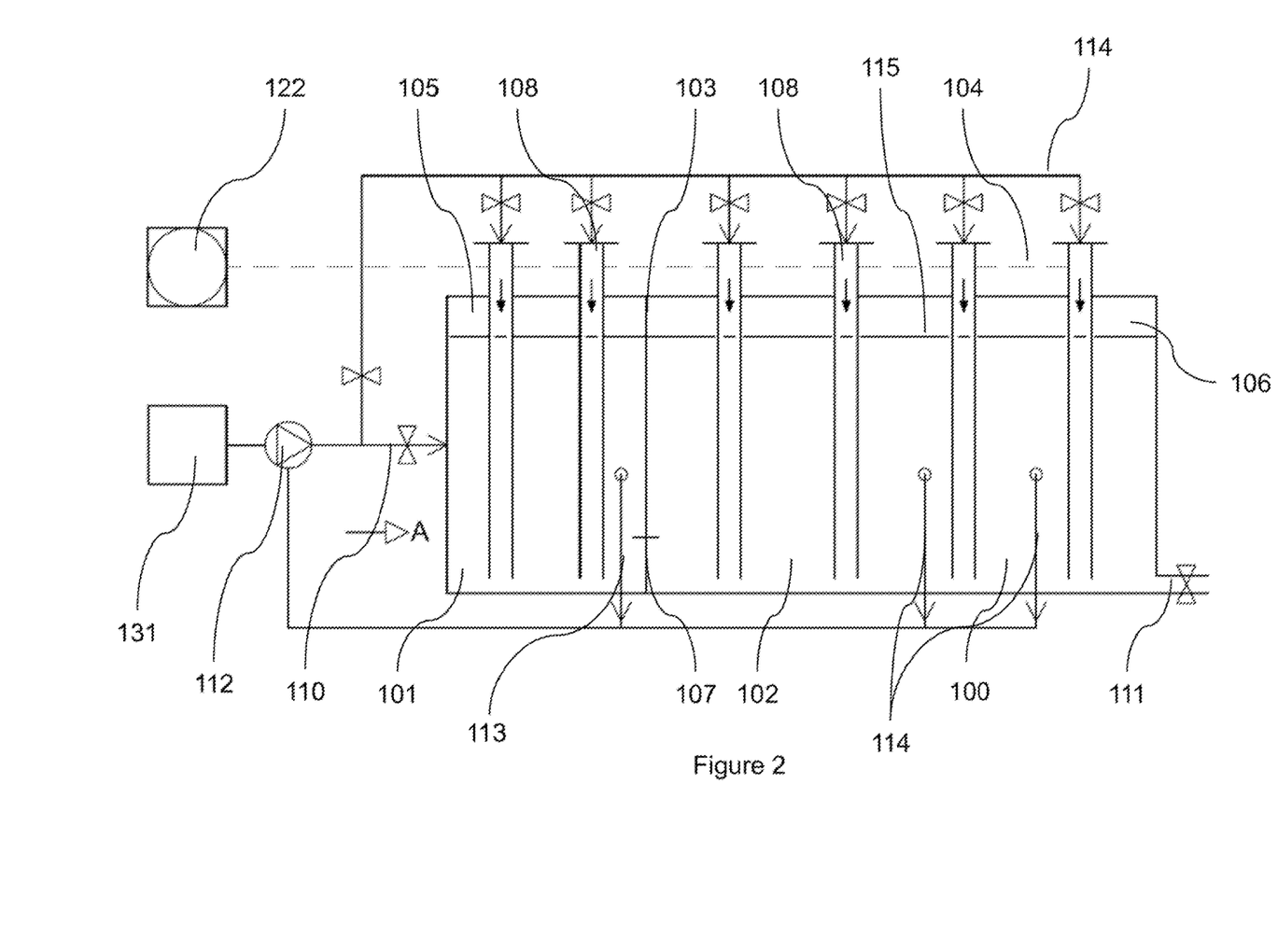
FIG. 2 represents, schematically, in a longitudinal cross-section, the first particular embodiment of the fermentation device that is the subject of the present invention.
Figure 3:
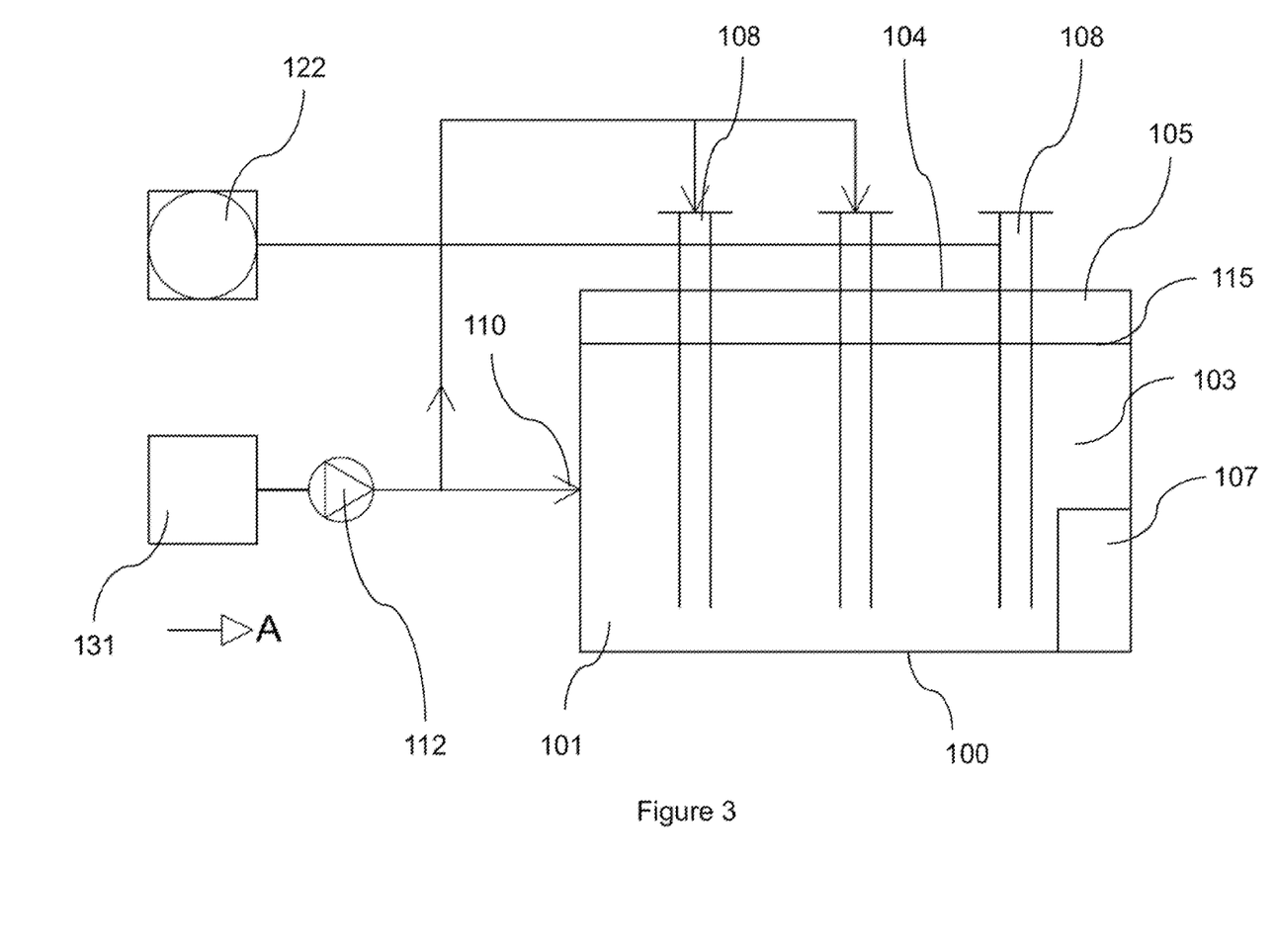
FIG. 3 represents, schematically, in a transversal cross-section, the first embodiment of the fermentation device that is the subject of the present invention.
Figure 4:
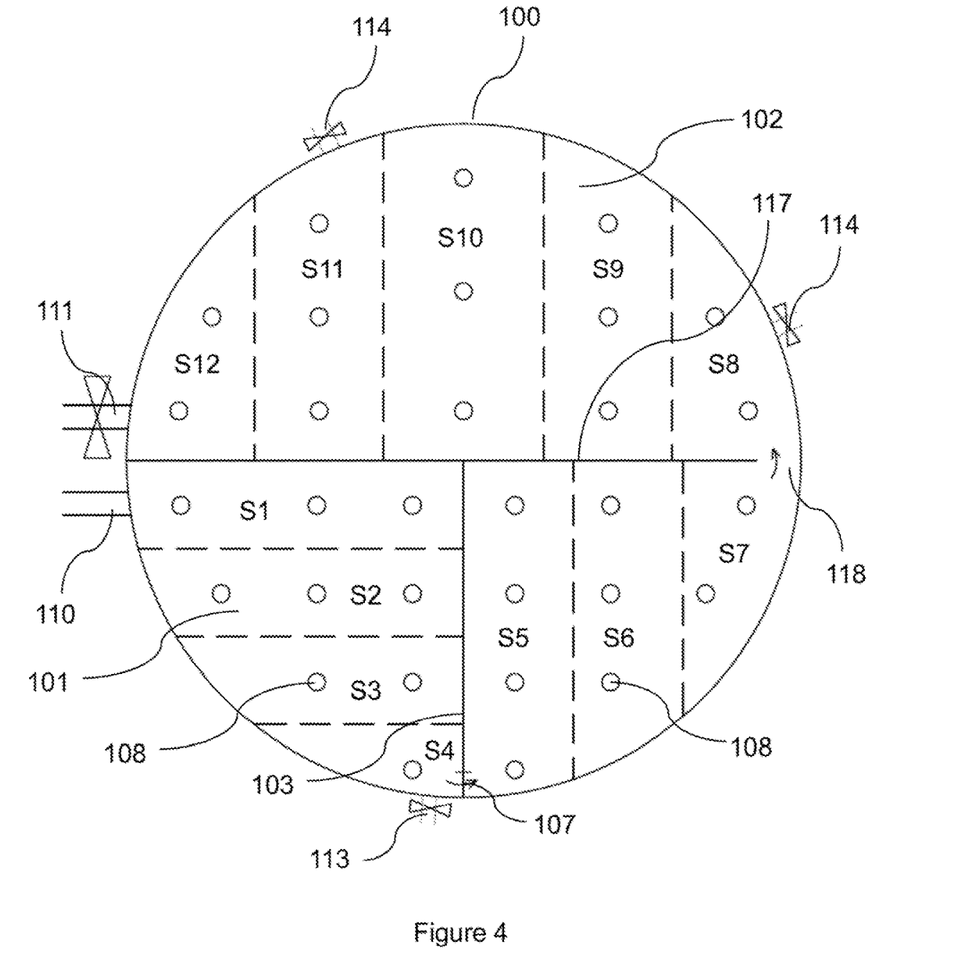
FIG. 4 represents, schematically, in a top view, a second embodiment of the fermentation device that is the subject of the present invention.

FIG. 4 presents a top view of the cylindrical fermenter separated into two compartments 101 and 102 separated by a wall 103 defining two atmospheres 105 and 106, and a partition 117 channeling matter over the second compartment 102 and leaving a passage 118 to allow the matter to pass over the second portion of the second compartment 102.

The chimneys 118 organized by four for sector S5, by three for sectors S1, S2, S4, S6, S7, S10, S11, S12, by two for sectors S3, S8, S9, S13, or singly close to zones of passage in the lower portion of the separation wall 103, sectors S4, S5 define mixing sectors where the mixing is to be controlled both over the height of matter as over the width of the floor of said sector by modifying the stirring itself through the speed and a variable flow rate, depending on the level of pressure in the chamber 122, the level of pressure depending on the duration of the compression, 8.5 minutes compression to raise to six relative bars and ten minutes compression to raise to seven relative bars. The gas is then released in 15 seconds, for example from six to four bars or from seven to five bars, which alters the speed and flow rate of the gas at the mouth of a chimney according to the number of chimneys. The speed and the flow rate can be modified at will and adjusted to the viscosity of the fermenting matter.

Figure 5:
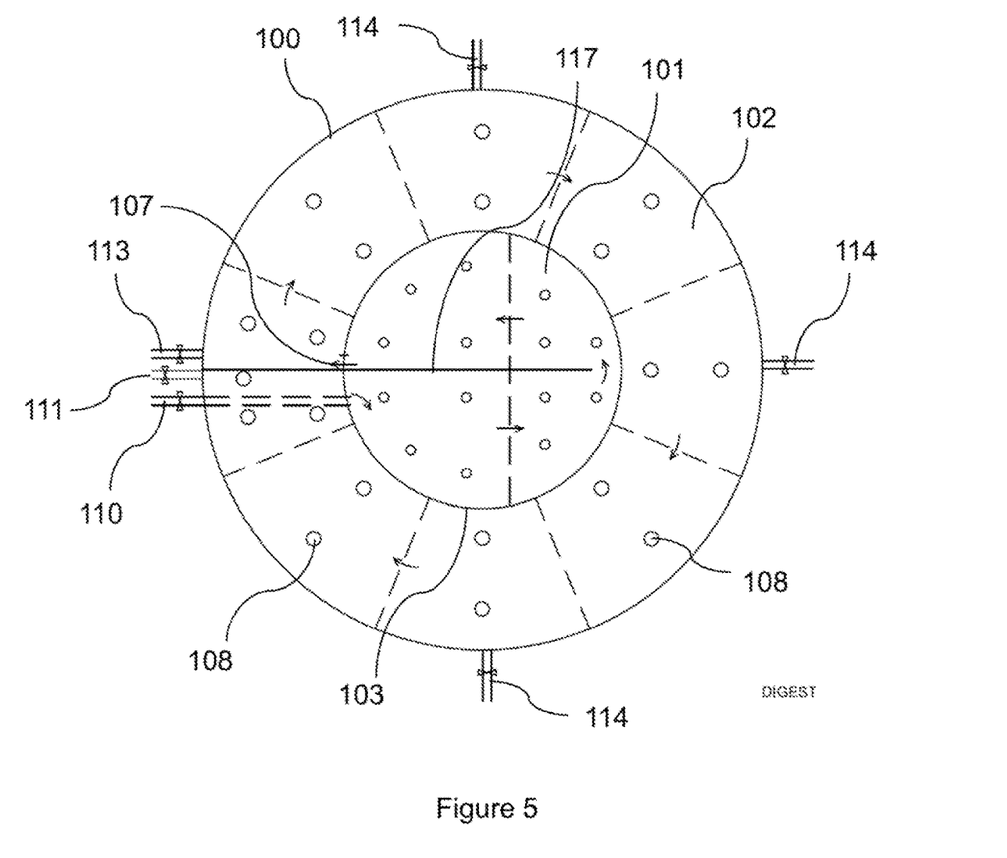
FIG. 5 represents, schematically, in a top view, a third embodiment with the first compartment incorporated into the second compartment of the fermentation device that is the subject of the present invention.
Figure 6:
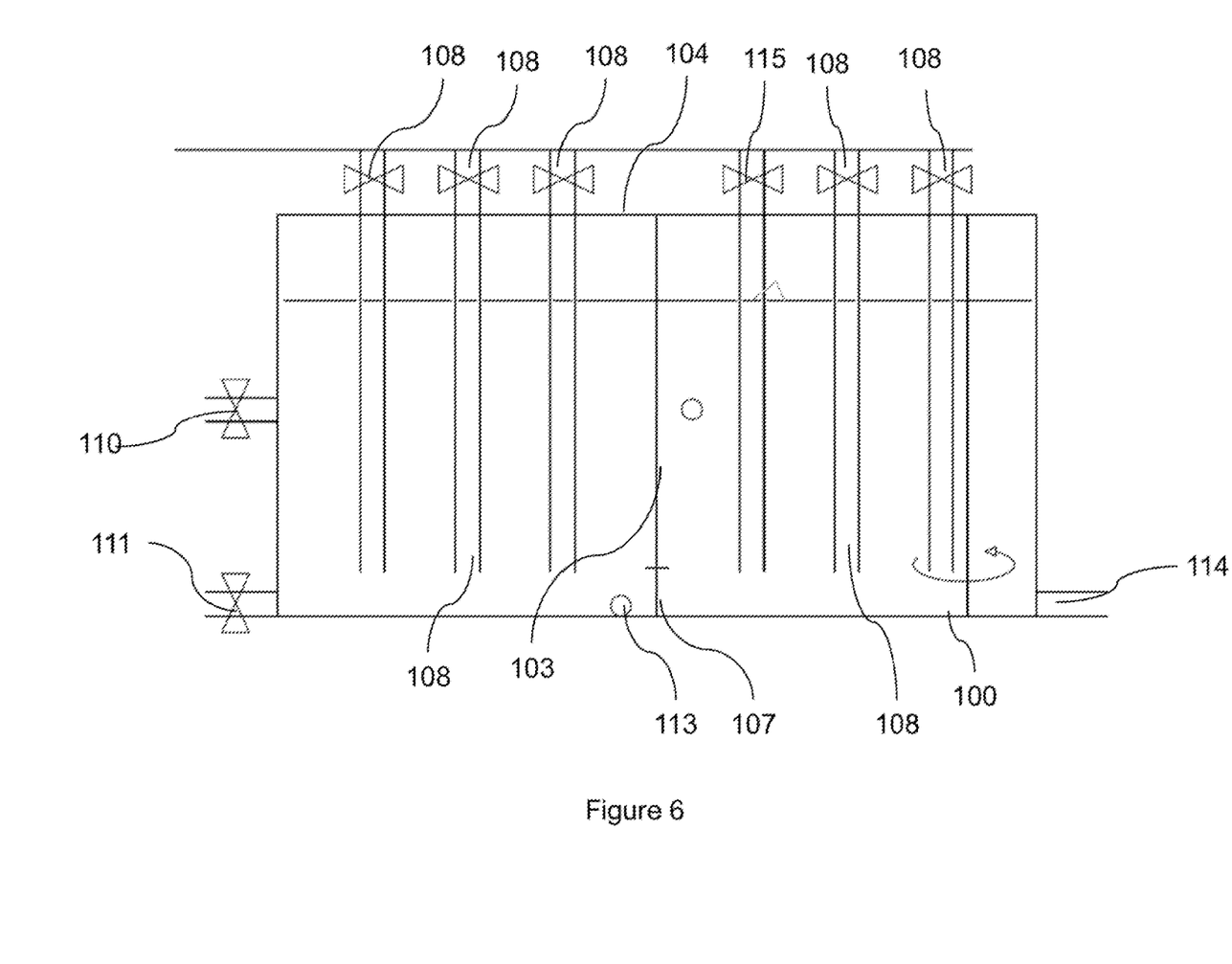
FIG. 6 represents, schematically, in a longitudinal cross-section, a fourth embodiment of the fermentation device that is the subject of the present invention.
Figure 7:
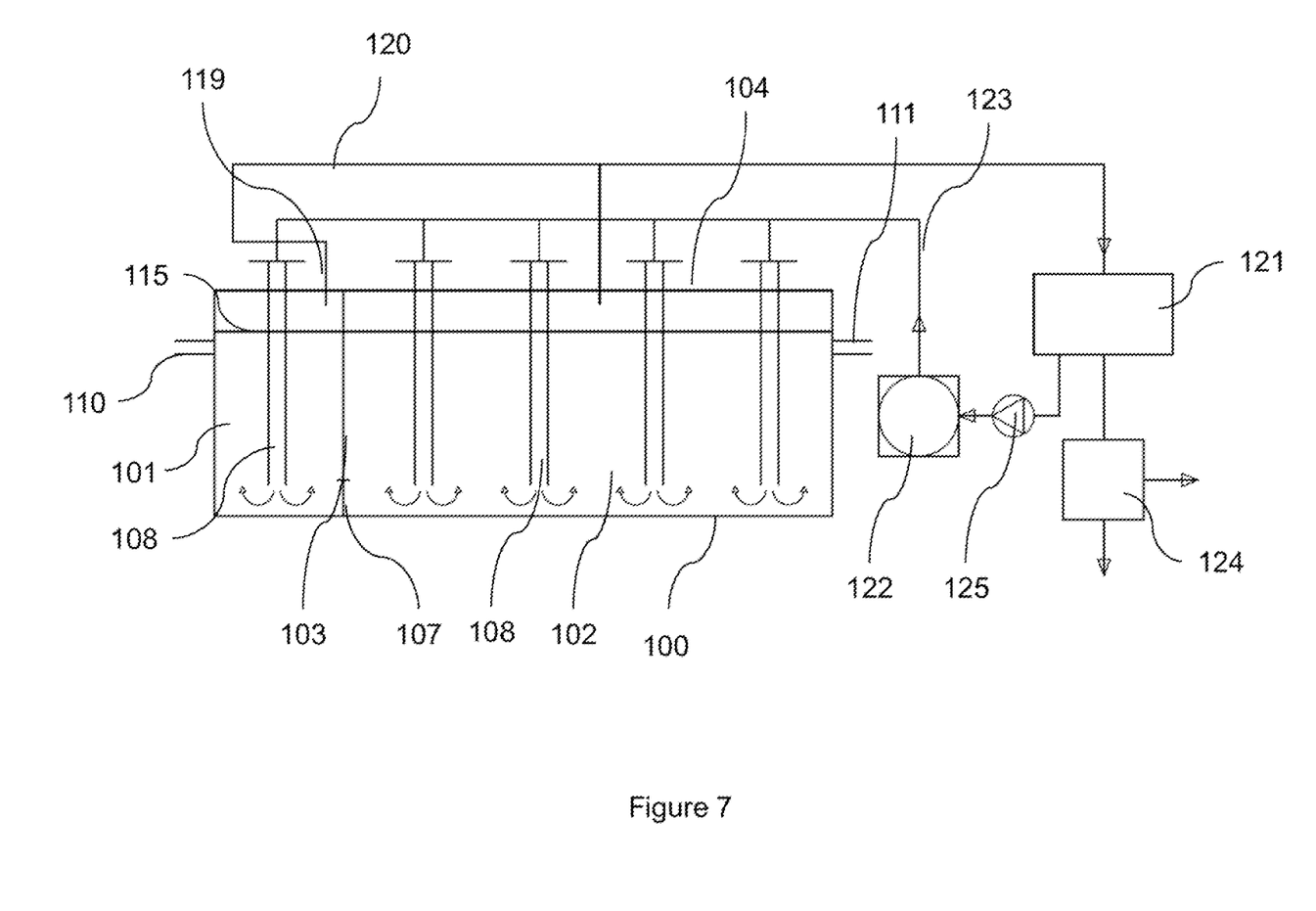
FIG. 7 represents, schematically, in a longitudinal cross-section, flows in particular embodiments of the fermentation device that is the subject of the present invention.

FIG. 5 presents a cylindrical fermentation device particularly suited to large fermenter volumes.

The device is based on two compartments 101 and 102 in a single vessel 100. The first thermo-enzymatic hydrolysis and acidogenesis compartment 101 is located inside a vessel 103, which serves as a wall between the two compartments 101 and 102. The matter is introduced by a slurry pump into the first sector S1 through a chimney 108 or directly into the tank by a channel linked to the slurry pump 122. The matter stirred sectorally by several chimneys 108, hydrolyzing thanks to the hyperthermophilic temperature, is moved in sectors S1 to S4, around the wall channeling the matter 117, to exit via a large passage 107 to continue its pathway by flowing in sectors S5 to S13 thanks to the high-flow-rate stirring by two chimneys in a plug flow, a flow made easier by the progressive solubilization of the matter to exit from the fermenter in the form of a digestate remaining thick in 111.

The device is also provided with control that is modeled and more or less automated depending on the type of installation. This control actuates, in a differentiated way, the speeds and flow rates of gas to be injected into the chimneys based on the level of pressure in the chamber at the start of the injection and the low level at the end of injection, as a function of the viscosity of the matter being set by the duration of stirring for a given volume, speed and flow rate of gas. This control also actuates the opening or closing of gas or matter valves and the recirculated quantities of matter at defined points of the fermenter by chimneys 108 or 201, depending on the fermenter's balance parameters (quality of the gas, pH, etc.) and on characteristics of the substrates to be fermented. This control of a set of gas or matter valves, more or less automated, makes it possible to modify the quantities to be recirculated in differentiated places in the fermenter as a function of gas or matter indicators that can be monitored in the two compartments 101 and 102 for the gas and from chimneys 108 or 201, for the matter at any place in the fermenter. The control indicators can be downloaded onto a central server, which sends back the fermenter's operational and control set points.

The method of continuous dry methanation, in a fermenter comprising a closed tank, comprises:
   a step of introducing slurry to be fermented, comprising at least 15% dry matter, into at least one compartment of said tank, and
   a step of injecting, via at least one chimney that descends through at least one said compartment, pressurized gas close to the bottom of the compartment, to create, by the injected gas rising through the slurry, a rising movement in the slurry around the chimney, stirring the matter that is found at the bottom of the compartment.

As described above, the slurry is introduced into a first compartment and, after hydrolysis in the first compartment, the hydrolyzed slurry is passed into a second compartment where methanogenesis takes place. The step of passing from the first compartment to the second is performed at the bottom of the tank, the atmospheres of the compartments thus not being in contact.

Preferably, during the gas injection, gas from the slurry's fermentation is introduced and gas is injected into at least two chimneys close to each other.

The method comprises, preferably, a step of measuring the viscosity of the slurry wherein, during the gas injection step, the quantity of gas, its flow rate and/or its speed are dependent upon the viscosity measured. For example, during the step of measuring the viscosity of the slurry, the slurry's resistance to the injection of gas is measured during the injection of gas. More specifically, during the step of measuring the viscosity of the slurry, a duration of a predefined drop in pressure of a volume of the injected gas is measured.

Preferably, the fermenter comprises a plurality of chimneys wherein, during the gas injection step, gas is injected successively into the chimneys. During the gas injection step, gas is injected successively into the chimneys going from upstream to downstream on the path followed by the slurry.

Preferably, during the gas injection step, a gas is injected into the slurry at a pressure at least five to ten times higher than the pressure of the height of the column of matter around the chimney.

Preferably, the method alternatively comprises:
a step of injecting gas into the slurry, and
a step of compressing biogas in a pressurized storage chamber.

For example, the cyclic ratio between the gas injection duration and the compression duration is less than one-thirtieth, e.g. between one-fiftieth and one-hundredth.

In embodiments, the method comprises a step of collecting slurry on the path followed by the slurry, and a step of injecting slurry upstream of the collection point.

The invention claimed is:

1. A device for fermenting a slurry by continuous dry methanation, the device comprising:
   a closed tank including at least a first compartment having an inlet configured to introduce therein slurry having at least 17% dry matter, and a second compartment having an outlet, said first and second compartments are separated by a wall extending from the top of the close tank and having a passage at a lower portion thereof allowing passage of hydrolyzed slurry from the first compartment to the second compartment,
   at least one chimney disposed in each of the first and second compartment, descending from the top of the compartment, and being configured to inject a pressurized gas close to a bottom of said compartment, wherein the injected pressurized gas rising through the slurry creates a convective movement in the slurry around said at least one chimney to stir the slurry at the bottom of the compartment; and
   a controller to command injection of the pressurized gas into the first and second compartments successively through each one of the chimneys;
   wherein said wall is configured to separate the first and second compartment such that atmospheres of the first and second compartments are not in contact with each other, said wall is further configured such that in the first compartment the slurry is hydrolyzed by said pressurized gas at a first temperature while in the second compartment methanogenesis of the hydrolyzed slurry is carried out at a second temperature lower than the first temperature.

2. The device according to claim 1, further comprising a pipe to introduce gas from the fermentation of the slurry to said at least one chimney.

3. The device according to claim 1, wherein said at least one chimney in said second compartment includes at least two chimneys in close proximity to each other.

4. The device according to claim 1, wherein said at least one chimney in said second compartment includes a plurality of chimneys wherein said controller is configured to command the injection of the pressurized gas successively into said plurality of chimneys from an upstream to a downstream on a path followed by the slurry.

5. The device according to claim 1, further comprising a sensor to measure a viscosity of the slurry; and a controller configured to control at least one of quantity, flow rate and speed of the injected pressurized gas in accordance with the measured viscosity of the slurry.

6. The device according to claim 5, wherein the sensor is configured to measure the slurry's resistance to the injection of the pressurized gas.

7. The device according to claim 1, further comprising a collector to collect a portion of the slurry at a collection point on a path followed by the slurry; and an injector configured to inject the collected portion of the slurry upstream of the collection point.

8. The device according to claim 1, wherein the pressurized gas that is injected into the slurry has a pressure at least five times higher than a pressure at a height of a column of the matter around said at least one the chimney, and at least 4 relative bars.

* * * * *